United States Patent [19]

Torossian et al.

[11] 4,098,804
[45] Jul. 4, 1978

[54] ESTERS OF 21-THIOL PREDNISONE AND PREDNISOLONE

[75] Inventors: Dieran Robert Torossian, Bourg-la-Reine; Gilbert Gustave Aubard; Jacky Marcel Legeai, both of Palaiseau, all of France

[73] Assignee: Jouveinal S.A., Val de Marne, France

[21] Appl. No.: 756,599

[22] Filed: Jan. 4, 1977

Related U.S. Application Data

[63] Continuation-in-part of Ser. No. 473,388, May 28, 1974, Pat. No. 4,014,909.

[30] Foreign Application Priority Data

May 30, 1973 [FR] France ................. 73 19734

[51] Int. Cl.$^2$ ............................................. C07J 31/00
[52] U.S. Cl. ........................... 260/397.45; 424/243
[58] Field of Search ..................... 260/397.45

[56] References Cited

U.S. PATENT DOCUMENTS

| | | | |
|---|---|---|---|
| 2,814,632 | 11/1957 | Nussbaum | 260/397.45 |
| 3,803,133 | 4/1974 | Vogt | 260/397.45 |
| 3,959,260 | 5/1976 | Phillipps et al. | 260/397.45 |

*Primary Examiner*—Elbert L. Roberts

*Attorney, Agent, or Firm*—Charles E. Baxley

[57] ABSTRACT

The present invention relates to new esters of the 21-thiol-steroids, having the general formula given at (I) below, and also to a method of preparation of these new esters.

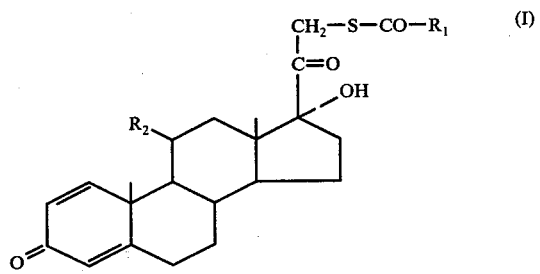

in which:
  $R_1$ represents an alkyl radical comprising a number of carbon atoms between 4 and 9, or the para-fluorophenyl radical;
  $R_2$ represents hydroxyl or the ketone function.

The esters of the invention have a considerable anti-inflammatory activity but also have small systemic effects and are applied especially to the local treatment of inflammatory illnesses.

29 Claims, No Drawings

ESTERS OF 21-THIOL PREDNISONE AND PREDNISOLONE

CROSS REFERENCE

The present application is a continuation in part application of application Ser. No. 473,388, filed May 28, 1974; now U.S. Pat. No. 4,014,909.

BACKGROUND OF INVENTION

The present invention relates to new esters of the 21-thiol steroids having the general formula(I)

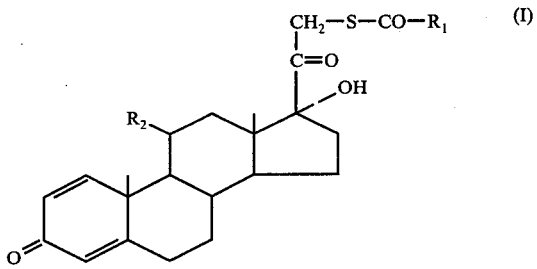

in which:
in which:

R$_1$ represents an alkyl radical comprising a number of carbon comprised between 4 and 9 atoms of carbon, or the parafluoro-phenyl radical;

R$_2$ represents hydroxyl or the ketone function

Several publications describe the modification of the group 21-hydroxyl-methyl of the corticoids, and more particularly the replacement of the oxygen of this function by sulphur.

Thus, the 21-thio-acetate of hydrocortisone is synthetized and declared free of any interesting biological activity (J. Org. Chem. 26, 1223, 1961).

Other derivatives have been proposed as anti-inflammatory products having solely a systemic action on the system or a local action and a systemic action:

The 21-thio-acetate and 21-thio propionate of prednisolone (U.S. Pat. No. 2,814,632) have been described as possessing an adreno-corticoid activity accompanied by considerable diuretic activity.

The 21-thio-acetate of dexamethasone (French Pat. No. 1187 M) has been proposed as an anti-inflammatory product with a local action and a systemic action.

The therapeutic use of corticoids having a systemic action generally gives rise to harmful "secondary effects" (Presse Medicale No. 31,1419–1423, 1970).

These secondary effects comprise mainly: endocrine troubles, sodium retention accompanied by a leakage of potassium, weakening of the defense reactions of the organism, which result in a pro-infection effect, digestive ulcers and disturbances of the glucidic, proteic and lipidic metabolisms.

The number and the variety of these secondary effects necessitate a certain prudence and careful supervision during the use of these products.

The present invention has for its object to find a remedy for these disadvantages.

STATEMENT OF INVENTION

It has been found that, in a surprising manner, the structures forming the object of the present invention comprising a thio-alkanoic group of high molecular weight, possess a considerable anti-inflammatory activity but they have only small systemic effects. The therapeutic doses thus remain very remote from those capable of causing the appearance of the secondary effects previously described.

Thus, certain substances according to the invention possess a thymolytic activity 200 times less than that of the glyco-corticoid of reference, whereas on the other hand their local anti-inflammatory activity is greater than that of the same reference.

Generally speaking, the substances forming the object of the present invention have shown a strongly reduced or nul activity on the glucidic and proteic metabolisms, little or no regression of the adrenal glands, no sodium retention.

In consequence, these substances are therapeutic agents having a very high safety in use, and this applies even in heavy doses, which find their application in the local treatment of inflammatory affections, such as the following:

Cutaneous illnesses and mucous illnesses that can be treated by corticoids;

Auto-rhino-laryngological and ophthalmological illnesses of an inflammatory and/or allergic nature;

Low digestive inflammations such as colities, recto-colities, and and recto-sigmoiditis;

Collagen troubles, articular and rhumatismal illnesses;

Asthma, emphysema and respiratory fibrosis.

In addition, and contrary to the corresponding non-sulphurous steroids, these products have a long period of action free from "rebound effect" which is of great interest in the treatment of chronic inflammatory illnesses.

According to the invention, the new esters of the 21-thiol steroids are prepared by condensation between:

on the one hand iodized derivatives having the general formula(II):

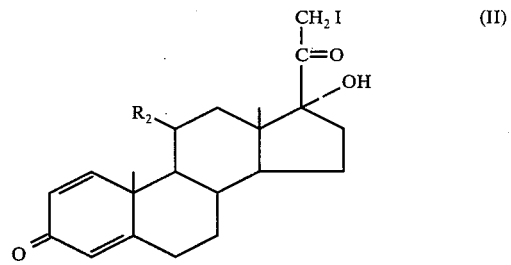

in which R$_2$ have the same signification as before;

on the other hand, S-thio-carboxylic acids utilised in their satisfied form, preferably in the form of the alkaline salts of these acids, especially the sodium salt.

As S-thio-carboxylic acids, there are employed acids such as:

The thio-alkanoic acids comprising a number of carbon atoms comprised between 5 and 10, for example the S-thio-pivalic acid, the S-heptanethioic acid, the S-decanethioic acid and the S-pentanethioic acid, the S-methyl-2 butanethioic acid, the S-methyl-3 butanethioic acid, the S-hexanethioic acid, the S-methyl-4 pentanethioic acid, the S-dimethyl-3.3 butanethioic acid, the S-ethyl-2 butanethioic acid, the S-octanethioic acid, the S-ethyl-2 hexanethioic acid, the S-nonanethioic acid.

The parafluoro S-thiobenzoic acid is also used.

In order to salify the S-thio-carboxylic acid, the procedure is preferably as follows:

The solvent, preferably anhydrous acetone, and the S-thio-carboxylic acids are introduced into the reactor, while stirring.

Then the sodium is introduced, preferably in the form of a methanol solution of sodium methylate, which is added drop by drop.

The operating conditions of the process of condensation of the iodized derivatives of Formula II and the alkaline S-thio-carboxylates are variable; however, the operation is generally carried out in the following manner:

There are introduced into a reactor comprising a reflux condenser, mechanical stirrer, the reaction solvent, especially anhydrous acetone, and then the iodized derivative of Formula II; to the suspension or solution thus formed there is added the acetone solution of the alkaline salt of S-thio-carboxylic acid previously prepared. The reaction medium is brought up to reflux and the solvent is then eliminated by distillation under vacuum.

It must be noted however that it is also possible to effect the condensation by introducing the iodized derivatives of Formula II in the powder form or in an acetone solution in the solution of sodium salt of S-thio-carboxylic acid and continuing the reaction as previously described.

The product obtained is purified depending on the case, either directly by crystallization from an alcohol having a low molecular weight or by column chromatography followed by a crystallization from the appropriate solvent or mixed solvents.

The molar ratio between the alkaline S-thio-carboxylate and the iodized derivative of Formula II employed is comprised between 1.4 mol of alkaline salt per mol of iodized derivative and 14 mols of alkaline salt per mol of iodized derivative.

The reaction temperatures are determined in dependence on the nature of the solvent and are in principle comprised between 56° and 102° C.

The time of the condensation reaction is favorably comprised between half an hour and 8 hours and preferably between 1 hour and 3 hours. For these reaction periods and according to the reactants utilized, the yields are substantially comprised between 12.5% and 90%. Generally speaking, the time of the reaction is determined in such manner as to limit the formation of secondary derivatives.

In order to define the characteristics of the ester of the 21-thiol steroids thus prepared, analytic chemical methods are utilized, such as functional analysis and elementary centesimal analysis, and physico-chemical methods such as the ultra-violet and infra-red spectra.

The method which has just been described in general terms has been utilized for a whole variety of radicals $R_1$; it will be seen in particular in connection with the non-limitative examples which follow below. These examples have been chosen in such manner as to define the utilization of the method according to the invention for at least one type of radical belonging to the families claimed hereinafter.

EXAMPLE 1

DIHYDROXY - 11β, 17 α THIOL 21 DIOXO - 320 PREGNADIENE - 1.4 - 21 PIVALATE (JO 1007).

In a 1 liter three necked round bottomed flask equipped with a dropping funnel, a mechanical stirrer and a calcium chloride tube to protect the apparatus from moisture, there are introduced successively 400 cu. cm. of anhydrous acetone and 28.36 grams of S-thiopivalic acid (0,24 mol.).

55.8 cu.cm. of a methanol solution of sodium methylate 3.58 M (0.2 mol) are introduced drop by drop in 12 minutes.

There is no modification of temperature, but the initial pale yellow colour becomes darker. After the introduction, stirring is continued for 5 minutes.

On the other hand, in a reactor of 10 liters fitted with a mechanical stirrer, a dropping funnel and a thermometer and a reflux condenser protected from moisture by a calcium chloride tube, there are introduced 6.4 liters of anhydrous acetone followed by 64 grams (0.136 mol) of dihydroxy-11β-17αiodo-21 dioxo-3.20 pregnadiene-1.4.

To this suspension, the acetone solution of sodium S-thiopivalate prepared above is introduced while stirring in 30 minutes. There is no change in temperature, the medium turns yellow and the product dissolves gradually.

The solution is brought up to the acetone reflux for 2 hours and then the solvent is eliminated by distillation under vacuum.

The yellow oily residue is poured into 1.2 liters of water, filtered and dried under vacuum at 40° C. The weight is 80 grams.

The product is purified by dissolving in 4 liters of boiling methanol and treatment of the solution with animal-charcoal.

After cooling, the very slightly yellow precipitate is filtered and dried under vacuum at 40° C.; weight 44.6 grams; yield 71.2%.

Analysis: $C_{26}H_{36}O_5S$: Calculated %: C, 67.80; H, 7.88; S, 6.96. Found %: C, 67.84; H, 7.90; S, 6.79.

Physical characteristics:

M.P. = 238° C.

$(\alpha)_D^{20}$ = + 118°, (dioxanne; c = 1%)

max. (methanol) at 239.5 mm, log.10 ε = 4.219

Main absorptions of infra-red spectrum -(KBr pellet): 1720, 1682, 1660, 1113, 895, 812, and 720 cm$^{-1}$

EXAMPLE 2

DIHYDROXY - 11β, 17α THIOL - 21 DIOXO - 3.20 PREGNADIENE - 1.4 - 21 HEPTANOATE (JO 1009)

In a 100 cu.em. three necked round bottomed flask equipped as described in Example 1, there are introduced 50 cu.cm. of anhydrous acetone, 4.36 grams of S-heptanethioic acid (0.03 mol) and finally 7.15 cu.cm. of methanol solution of sodium methylate 3.5 M (0.025 mol).

On the other hand, in a two liters three necked round bottomed flask equipped as described in Example 1, there are introduced 800 cu.cm. of anhydrous acetone and 8 grams of dihydroxy-11β, 17α iodo-21 dioxo-3.20 pregnadiene-1.4 (0.017 mol).

The solution of sodium S-heptanethioate obtained above is introduced to the suspension and there is observed the gradual dissolving of the product. After two hours reflux, the solution is treated as in Example 1.

The residue is purified by recrystallization from 60 cu.cm. of methanol: weight = 4.85 grams; yield: 58%.

Analysis $C_{28}H_{40}O_5S$: Calculated %: c, 68.82; H, 8.25; S, 6.56. Found %: C, 68.71; H, 8.15; S, 6.61.

Physical characteristics

M.P. = 159° C $(\alpha)_D^{20}$ = + 101°, (dioxanne: = 1.25%)

max. (methanol) at 237.5 mm, log.$_{10}$ ε = 4.236

Main absorptions of infra-red spectrum - (KBr pellet): 1725, 1695, 1655, 1600, 1232, 1135, 1112, 895, 830 and 720 cm$^{-1}$

EXAMPLE 3

DIHYDROXY - 11 $\beta$, 17 $\alpha$ THIOL - 21 DIOXO - 3.20 PREGNADIENE - 1.4 21 DECANOATE (JO 1050)

Carrying out the operation under the same conditions as in EXAMPLE 1, from 5.16 grams of S-decanethioic acid (27.4 mmols), 7.2 cu.cm. of sodium methylate solution 3.8 N (27.4 mmols) and 10.72 grams of dihydroxy-11$\beta$, 17$\alpha$ iodo-21 dioxo-3.20 pregnadiene-1.4 (22.8 mmols), there are obtained after treatment and crystallisation from methanol 9.2 g of white product. Yield = 76%.

Analysis $C_{31}H_{46}O_5S$: Calculated %: C, 70,16; H, 8,74; S, 6.04. Found %: C, 70.04; H, 8.60; S, 5.90.

Physical characteristics
M.P. = 160°–163° C
$(\alpha)_D^{20}$ = + 110°, (dioxanne, c = 1%)
$\lambda$ max. (methanol) at 236 mm, $\log_{10} \epsilon$ = 5,255

Main absorbtions of infra-red spectrum (KBr pellet): 2920, 2850, 1650, 1590, 1245, 1130, 1110, 895 and 720 cm$^{-1}$ By proceeding in the manner of EXAMPLE 1, but with S-thioalkanoics acids indicated in Column 1 below the thio esters of Column 2 are obtained.

| COLUMN 1 | COLUMN 2 |
| --- | --- |
| S - pentanethioic acid | dihydroxy-11$\beta$, 17$\alpha$ thiol-21 dioxo-3.20 pregnadiene - 1.4 21 pentanoate |
| S - methyl-2 butanethioic acid | dihydroxy-11$\beta$, 17$\alpha$ thiol-21 dioxo-3.20 pregnadiene - 1.4 21 methyl-2 butanoate |
| S - methyl-3 butanethioic acid | dihydroxy-11$\beta$, 17$\alpha$ thiol-21 dioxo-3.20 pregnadiene - 1.4 21 methyl-3 butanoate |
| S - hexanethioic acid | dihydroxy-11$\beta$, 17$\alpha$ thiol-21 dioxo-3.20 pregnadiene - 1.4 21 hexanoate |
| S - methyl-4 pentanethioic acid | dihydroxy-11$\beta$, 17$\alpha$ thiol-21 dioxo-3.20 pregnadiene - 1.4 21 methyl 4 - pentanoate |
| S - dimethyl-3.3 butanethioic acid | dihydroxy-11$\beta$, 17$\alpha$ thiol-21 dioxo-3.20 pregnadiene - 1.4 21 dimethyl-3.3 butanoate |
| S - ethyl-2 butanethioic acid | dihydroxy-11$\beta$, 17$\alpha$ thiol-21 dioxo-3.20 pregnadiene - 1.4 21 ethyl-2 butanoate |
| S - octanethioic acid | dihydroxy-11$\beta$, 17$\alpha$ thiol -21 dioxo-3.20 pregnadiene - 1.4 21 octanoate |
| S - ethyl-2 hexanethioic acid | dihydroxy-11$\beta$, 17$\alpha$ thiol-21 dioxo-3.20 pregnadiene - 1.4 21 ethyl-2 hexanoate |
| S - nonanethioic acid | dihydroxy-11$\beta$, 17$\alpha$ thiol-21 dioxo-3.20 pregnadiene - 1.4 21 nonanoate |

EXAMPLE 4

DIHYDROXY - 11$\beta$, 17$\alpha$ THIOL - 21 DIOXO - 3.20 PREGNADIENE - 1.4 - 21 p. FLUORO BENZOATE (JO. 1014)

Under the same conditions as in EXAMPLE 1, starting from 4.68 grams of S-p. fluoro-thio-benzoic acid (0.03 mol) and 6.85 cu.cm of sodium methylate sodium 3.66 M (0.025 mol) on the one hand and 8 grams of dihydroxy-11$\beta$, 17$\alpha$ iodo-21 dioxo 3.20 pregnadiene-1.4 (0.017 mol) on the other hand, there is obtained ater treatment 9.8 grams of crude product which is purified by crystallization from 50 cu.cm. of methanol; weight: 4.55 grams; yield: 53.7%.

Analysis: $C_{28}H_{31}FO_5S$: Calculated %: C, 67.45; H, 6.27; F, 3.81; S, 6.43. Found %: C, 67.33; H, 6.14; F, 3.63; S, 6.41.

Physical characteristics:
M.P. = 240°–245° C
$(\alpha)_D^{20}$ = + 150° (dioxanne, c = 0.3%)
$\lambda$ max. (methanol) at 233 nm $\log_{10} \epsilon$ = 4.576

Main absorptions of infra-red spectrum, - (KBr pellet): 1718, 1655, 1590, 1505, 1232, 1210, 1160, 1120, 920, 850 and 720 cm$^{-1}$

EXAMPLe 5

HYDROXY - 17 $\alpha$ THIOL - 3,11,20 PREGNADIENE - 1.4 - 21 PIVALATE (JO 1032)

In a 250 cu.cm. three necked bottomed flask equipped with a mechanical stirrer, a dropping funnel and a calcium chloride tube, there are introduced 52 cu.cm. of anhydrous acetone and 2.81 grams of S-thiopivalic acid (23.8 mol).

5.1 cu.cm. of methanol solution of sodium methylate 3.9 M (19.8 mols) are introduced drop by drop in three minutes. The reaction medium is left for 15 minutes while stirring.

In the other hand, in a balloon flask of 1 liter fitted with a mechanical stirrer, a dropping funnel, a theromether and a reflux condenser protected from moisture by a calcium chloride tube, 630 cu.cm. of anhydrous acetone and 6.3. grams (13.5 mmols) of hydroxy-17$\alpha$ iodo-21 trioxo-3,11, 20 pregnadiene-1.4 are introduced After 15 minutes stirring at the laboratory temperature, a yellow solution is obtained into which there is introduced the acetone solution of sodium S-thiopivalate prepared above. The introduction is effected drop by drop in 15 minutes without variation of temperature.

The reaction medium is brought up to the reflux of the acetone for 2 hours, and the solvent is then eliminated by distillation under vacuum.

The solid yellow residue obtained is scrapped in 200 cu.cm. of distilled water, filtered and dried under vacuum at 40° C. — weight 5.75 grams.

The product is purified by crystallization from 750 cu.cm. of methanol. After cooling, the yellow precipitate is filtered and dried under vacuum at 40° C; weight = 3.5 grams; yield = 56.3 %.

Analysis: $C_{26}H_{34}O_5S$: Calculated %: C, 68.09; H, 7.47; S, 6.99. Found %: C, 67.95; H, 7.53; S, 6.92.

Physical characteristics:
M.P. = 237°–240° C
$(\alpha)_D^{20}$ = + 182.5° (dioxanne; c = 1%)
$\lambda$ max. (methanol) at 235 nm, $\log_{10} \epsilon$ = 4.247

Main absorptions of infra-red spectrum (KBr pellet) 1705, 1655, 1610, 1365, 1045, 960, 895, 810 and 700 cm$^{-1}$

EXAMPLE 6

HYDROXY - 17$\alpha$ THIOL - 21 TRIOXO - 3,11,20 PREGNADIENE - 1.4 - 21 HEPTANOATE (JO 1033)

The sodium S-heptanethioate is prepared in the usual manner from 8.58 grams (58.7 mmols) of S-heptanethioic acid, 12,5 cu.cm. of methanol solution of sodium methylate 3.9 M (49 mmols) in 100 cu.cm. of anhydrous acetone.

The acetone solution is introduced into a solution of 15.6 grams (33.3 mmols) of hydroxy-17 $\alpha$ iodo-21 trioxo-3,11,20 pregnadiene-1.4 in one liter of acetone.

The reaction and the treatment are carried out following the usual method. The crude product obtained is purified by crystallization from an ethanol-petroleum ether mixture; weight: 4.5 grams; yields: 27.6%.

Analysis: $C_{28}H_{40}O_5S$: Calculated %: C, 69.10; H, 7.87; S, 6.59. Found %: C, 69.25; H, 7.95; S, 6.47.

Physical characteristics:
M.P. inst. = 150°–151° C.
$(\alpha)_D^{20} = +170°$; (dioxanne; c = 1%)
$\lambda$ max. (methanol) at 232 nm, $\log_{10} \epsilon = 4.3475$
Main absorptions of infra-red spectrum (KBr pellet): 1700, 1655, 1610, 1370, 1305, 1240, 1045, 895 and 700 $cm^{-1}$

EXAMPLE 7

HYDROXY - 17 THIOL described 21 TRIOXO - 3,11,20 PREGNADIENE 1,4 - 21 DECANOATE (JO 1051)

Under the same conditions as in Example 5, starting from 5.18 grams of S-decanethioic acid (22.9 mmols), 7.25 cu.cm. of sodium methylate solution 3.8 N (27.5 mmols) and 10.72 grams of hydroxy-17 iodo-21 trioxo-3,11,20 pregnadiene-1.4 there are obtained after isolation of crude product and crystallisation from methanol 8.6 g of purified product; yield: 71%.

Analysis: $C_{31}H_{44}O_5S$: Calculated %: C, 70,42; H, 8,39; S, 6,06. Found %: C, 70,23; H, 8,38; S, 6,06.

Physical characteristics
M.P. = 107°–110° C
$(\alpha)_D^{20} = +152°$ (dioxanne, c = 1%)
$\lambda$ max. (methanol) at 236 nm; $\log_{10} \epsilon = 5,276$
Main absorptions of infra-red spectrum (KBr pellet): 2920, 2850, 1690, 1655, 1360, 1240, 890 and 695 $cm^{-1}$ By proceeding in the manner of EXAMPLE 5, but with S-thioalkanoics acids indicated in Column 1 below the thio esters of Column 2 are obtained.

| COLUMN 1 | COLUMN 2 |
|---|---|
| S - Pentanethioic acid | Hydroxy-17α thiol-21 trioxo-3,11, 20 pregnadiene 1.4 21 pentanoate |
| S - Methyl-2 butanethioic acid | Hydroxy-17α thiol-21 trioxo-3,11, 20 pregnadiene 1.4 21 methyl-2 butanoate |
| S - Methyl-3 butanethioic acid | Hydroxy-17α thiol-21 trioxo 3,11, 20 pregnadiene 1.4 21 methyl-3 butanoate |
| S - Hexanethioic acid | Hydroxy-17α thiol-21 trioxo 3,11, 20 pregnadiene 1.4 21 hexanoate |
| S - Methyl-4 pentanethioic acid | Hydroxy-17α thiol-21 trioxo 3,11, 20 pregnadiene 1.4 21 methyl-4 pentanoate |
| S - Dimethyl-3.3 butanethioic acid | Hydroxy-17α thiol-21 trioxo 3,11, 20 pregnadiene 1.4 21 dimethyl-3.3 butanoate |
| S - Ethyl-2 butanethioic acid | Hydroxy-17α thiol-21 trioxo 3,11, 20 pregnadiene 1.4 21 ethyl-2 butanoate |
| S - Octanethioic acid | Hydroxy-17α thiol-21 trioxo 3,11, 20 pregnadiene 1.4 21 octanoate |
| S - Ethyl-2 hexanethioic acid | Hydroxy-17α thiol-21 trioxo 3,11, 20 pregnadiene 1.4 21 ethyl-2 hexanoate |
| S - Nonanethioic acid | Hydroxy-17α thiol-21 trioxo 3,11, 20 pregnadiene 1.4 21 nonanoate |

EXAMPLE 8

HYDROXY - 17α THIOL - 21 TRIOXO - 3,11,20 PREGNADIENE - 1,4 - 21 p. FLUOROBENZOATE (JO 1047)

Under the same conditions as in Example 5, starting from 4.30 grams of S p. fluoro-thio-benzoic acid (27.5 mmols), 7.25 cu.cm. of sodium methylate solution 3.8 N (27.5 mmols) and 10.72 g of hydroxy-17α iodo-21 trioxo-3,11,20 pregnadiene-1.4 (22.9 mmols), there is obtained after treatment 9.35 g of crude product which is purified by crystallisation from methanol; weight = 6.9 grams. Yield: 60%.

Analysis: $C_{28}H_{29}FO_5S$: Calculated %: C, 67,72; H, 5,89; F, 3,83; S, 6.46. Found %: C, 67,72; H, 5,89; F, 3,79; S, 6,41.

Physical characteristics
M.P. = 185°–188° C
$(\alpha)_D^{20} = +210°$ (dioxanne, c = 1%)
$\lambda$ max. (methanol) at 238 nm $\log_{10} \epsilon = 5,423$
Main absorptions of infra-red spectrum (KBr pellet): 3550, 2940, 1660, 1600, 1500, 1205 and 920 $cm^{-1}$

PHARMACOLOGICAL STUDY

There will now be described the tests which have enabled the determination of the pharmaco-dynamic properties of the esters of the 21-thiols steroids according to the invention.

ANTI-INFLAMMATORY ACTIVITY

The experimental local anti-inflammatory activity of the compounds presented was estimated in rats by their anti-proliferative (anti-granulomatous) action, and for one of these, by its anti-arthritic activity and its anti-exudative activity.

(a) ANTI-PROLIFERATIVE ACTIVITY

The anti-proliferative (anti-granulomatous) activity has been brought into evidence by means of a test, the principle of which is as follows.

The introduction of a foreign body into an organism produces a set of inflammatory reactions which results, in the chronic stage, in the formation of a defence granuloma around the foreign body. The proliferation of this granuloma is eliminated or attenuated by anti-inflammatory agents.

The technique employed is very similar to that described by Winter and Porter (J. Am. Pharm. Ass. 46/9. 515 1957) with rats.

Homogeneous groups of 10 male adult rats of the Wistar Strain were used, distributed at random and having weights comprised between 180 and 200 grams.

The implants or pellets were prepared from rolls of dental cotton; the weight of the pellets was between 35 and 40 mg.

Immediately before their introduction, the pellets were soaked with an antibiotic solution (0.1 ml. of a solution of penicillin G and streptomycin containing 200 000 UI of penicillin G and 0.1 gram of steptomycin sulphate per cc.).

Each animal received two pellets in the sub-cutaneous dorsal tissue on each side of the spinal column, at the costo-lumbar angle, under light anaesthesia with ether. The day of the operation and for three days after, the animals received by sub-cutaneous injection, 0.1 ml. of the antibiotic solution in the caudal region.

Six days after the introduction, the animals were killed by inhalation of chloroform and the granulomae were extracted and weighed, (wet and dry), and then the initial weights of the cotton pellets were substracted from the total weight.

Certain non-sulphured steroids causing a large increase in protein catabolism which can influence the formation of the granuloma independently of their antiinflammatory action, the weights of the granulomae were expressed as a percentage of the body weight (technique proposed by G. Dipasquale and A. Meli: J. Pharm. Pharmacol. (1965), 17, 367–382) and the anti-proliferative effect of the various compounds as a percentage inhibition with respect to the reference granulomae. The $ED_{50}$ were calculated by transferring the results on semi-logarithmic paper.

(a - 1) Local Anti-inflammatory Activity

For this study, the products to be tested were dissolved in chloroform or in dimethylsuphoxide (DMSO) and the solutions obtained, deposited on the pellets at a volume of 0.2 ml per pellet. The solvent was then evaporated under high vacuum at ambient temperature, the complete elimination of the solvent being checked by weighing the pellets. "Reference" pellets, soaked with the solvent alone, were treated in the same manner.

(a - 2) Systemic Anti-inflammatory Activity

For this study, each animal received two untreated pellets. The product are given by oral route, daily during 6 days; the first administration began about two hours after the implanation.

The products were administered in suspension in a solution of arabic gum at 5% (w/v), at a volume of 1 ml/rat.

(b) Anti-arthritic Activity

The anti-arthritic activity was brought out by means of a test, the principle of which is as follows:

This test was carried out following a method derived from that described by Foldi-Borcsok and Coll. (Arzneimittel Forschung 21, 2025–2030, 1971).

The injection of kaolin in the tibio-metatarsal joint of the rat causes an inflammation which develops in two successive phases:
 an acute phase characterized by an oedema of the joint;
 a chronic phase which follows, characterized by the proliferation of an inflammatory granuloma.

The intensity of the inflammatory reaction is estimated following the width of the articulation.

Male rats of Wistar stock were utilized, the initial weight of which was between 180 and 200 grams. Each group comprised ten animals taken at random, in which the width of the right-paw tibio-metatarsal joint was measured to the nearest 1/20th of a millimeter.

All the animals received 0.05 ml. of suspension of kaolin at 10% in a 0.9% physiological solution by intra-articular injection in the right-paw tibio-metatarsal joint.

Eighteen hours after this injection, the width of the joint was measured (initial inflammation) and there was then carried out an intra-articular injection of the products under study, in suspension in 0.5% carboxy-methyl-cellulose at a volume of 0.05 ml. The animals belonging to the control lot received 0.05 ml of the vehicle by the same method.

Twenty-four hours after this last injection, the width of the joint treated was again measured and then daily for 9 or 10 days, according to the evolution of the animals of the control group.

The variation of width of the joints treated, representing the anti-arthritic activity of the products under study, were expressed as a percentage of the initial inflammation according to the formula:

Anti-arthritic activity on the Nth day =

$$\frac{\Delta_1 - \Delta_n}{\Delta_1} \times 100$$

in which:
 $\Delta_1$ = increase in width of the joint with respect to its initial width, during the initial inflammation;
 $\Delta_n$ = increase in width of the joint with respect to its initial width, on the day considered.

The calculations were carried out by using the averages of the individual results of each lot.

SYSTEMIC EFFECTS

The systemic effects of the compounds according to the invention were evaluated through the intermediary of their thymolytic activity and for some of these, their possible influence on the glucidic metabolism, the hydro-mineral equilibrium, the weight increase, the endocrine glands and the genital tractus was examined and also a possible ulcerogenic effect.

(c) Thymolytic Effect

The thymolytic effects have been examined by means of a test, the principle of which is as follows:

The repeated administration of a gluco-corticoid having a systemic activity causes an involution of the defence system of the organism, of which two organs belong to the reticuloendothelial system, the spleen and the thymus, this latter being the most sensitive to this action, especially with young animals. The thymic involution is estimated by weighing.

The thymolytic effects was studied by two routes:
1. local route (local effects)
2. oral route (systemic effects)

(c - 1) Local Effects

For this study, the products are administered locally on pellets, following the procedure $a_1$.

Six days after implanation, the thymus are taken off and quickly weighed.

(c - 2) Systemic Effects

For this study, the various products were injected daily by the oral or the sub-cutaneous route for 4 days, to young male rats of Wistar-strain, the initial weight of which was between 45 and 55 grams, distributed at random by groups of 10.

The products under study were administered at a volume of 0.2 ml. per animal for both routes, in suspension in:
 Carboxy-methyl-cellulose at 0.5% for sub-cutaneous injection;
 Gum arabic at 5% for the oral route.

The animals of the control groups received the same volume of the corresponding vehicle.

Ninety-six hours after the first administration, the animals were killed, the thymus glands being taken and weighed immediately.

For each animal, the weight of the thymus has been brought to 100 grams of body weight. The thymolytic activity of the products under study was then expressed as a percentage of regression of the thymus with respect to the animals of the control group and the $ED_{50}$ of each product tested was estimated by transferring the percentage inhibition obtained for each dose on semi-logarithmic paper.

(d) Action on the Protein Metabolism

The action on the protein metabolism was examined by means of a test, the principle of which is as follows:

The administration of gluco-corticoids results in a disturbance of the protein metabolism, which is shown by an exaggerated protein catabolism resulting in shrinking of the tissues objectified by an inhibition of growth in weight in the young animal and a loss of body weight in the adult animal.

(d - 1) After a Short Term Study

For this study, immature rats of Wistar strain were utilized, the initial weight of which was between 45 and 55 grams, which were distributed at random groups of 10.

(d - 1.1.) Local Activity

For this study, the products are administered locally on pellets, like the described procedure in $a_1$. The animals are weighed before the implantation and six days after.

(d - 1.2.) Systemic Activity

The products were administered daily for 6 days. The animals were weighed daily during the four days of treatment and 24 hours after the last dose.

The products tested were administered by orally injection in suspension of 5% arabic gum, the animals of the control group receiving the same volume of vehicle by the same method as the corresponding animals treated.

The average variation of the body weight during the 144 hours treatment was calculated for each group of animals.

(e) Action on the Adrenals

The administration of corticoids may result in an inhibition of the secretion of the ante-hypophysiary hormone which is shown by a lowering of the effectiveness of the target glands: adrenals.

This effect was evaluated after a short or a long term study.

(e - 1.) Local Effect

The products are administered locally on pellets following the described procedure $a_1$.

Six days after implanation, the adrenals are taken off and quickly weighed.

(e - 2.) Systemic Effects

The products are administered daily during 6 days. The products given are in suspension in a solution of arabic gum at 5% (w/v) by oral route, under a volume of 1 ml/rat.

The day after the last administration, the adrenals are taken off and quickly weighed.

RESULTS OF PHARMACOLOGICAL STUDY

There will now be described the results of the pharmacological study.

(a) ANTI-PROLIFERATIVE ACTIVITY (a - 1) Local Anti-inflammatory Activity

The obtained $ED_{50}$ for each of the presented products and their corresponding steroids are indicated in TABLE I.

TABLE I

| | DERIVATIVES OF PREDNISOLONE OR PREDNISONE | |
|---|---|---|
| TREATMENT | WET WEIGHT OF PELLET | DRY WEIGHT OF PELLET |
| Prednisolone (base) | $ED_{50}$ = 4 mg/pellet | $ED_{50}$ = 2 mg/pellet |
| Prednisolone (acetate) | $ED_{50}$ = 2 mg/pellet | $ED_{50}$ = 1,2 mg/pellet |
| JO 1007 | $ED_{50}$ = 0,44 mg/pellet | $ED_{50}$ = 0,20 mg/pellet |
| JO 1009 | $ED_{50}$ = 0,50 mg/pellet | — |
| JO 1014 | $ED_{50}$ = 0,5 mg/pellet | $ED_{50}$ = 0,12 mg/pellet |
| JO 1032 | $ED_{50}$ = 5,6 mg/pellet | $ED_{50}$ = 0,12 mg/pellet |

(a - 2) Systemic Anti-inflammatory Activity

The obtained $ED_{50}$ are indicated in the TABLE II:

TABLE II

| | DERIVATIVES OF PREDNISONE | |
|---|---|---|
| TREATMENT | WET WEIGHT OF PELLET | DRY WEIGHT OF PELLET |
| Prednisone acetate | $ED_{50}$ = 108 mg | $ED_{50}$ = 5,4 mg |
| JO 1032 mg/Rat | $ED_{50}$ > 750 mg | $ED_{50}$ > 750 mg |

The $ED_{50}$ are expressed as the total dose administered during six days, per rat.

Under the conditions of this test, when administered in a dose of 125 mg/rat/day compound JO 1032 is free of antiinflammatory activity, contrary to prednisolone acetate the $ED_{50}$ of which is 0,9 mg/rat/day.

(b) ANTI-ARTHRITIC ACTIVITY

The results indicated in TABLE III represent the anti-arthritic activity of one product and its reference steroid; this activity is estimated from the diminution in width of the joint (as a percentage of the initial inflammation), 24 hours after the injection and 120 hours after the injection.

The product and its reference are administered in a ratio of doses equal to the ratio of their respective molecular weights.

TABLE III

| | DOSE | 24 Hours | 120 Hours |
|---|---|---|---|
| Prednisolone base | 1 mg | − 57.7% | − 1.9% |
| JO 1007 | 1.278 mg | − 62.4% | − 77.3% |

When administered by local route, compound JO 1007 exerts an anti-arthritic activity similar to that of prednisolone, during the first 24 hour period. However, in the case of compound JO 1007, the effect persists during 120 hours whereas, at the end of the same period, prednisolone does not cause any further effect.

(c) THYMOLYTIC ACTIVITY (c - 1) Local Activity

The thymolytic activity by local route is expressed in the TABLE IV.

TABLE IV

| TREATMENT | NUMBER OF RATS | WEIGHT OF THYMUS Mean (MG) ± e.s. | % AND PROBABILITIES |
|---|---|---|---|
| CONTROL | 10 | 308,7 ± 13,10 | — |
| JO 1032 0,01 mg/pellet | 10 | 331,9 ± 12,14 | + 7,5 N.S. |
| JO 1032 0,05 mg/pellet | 10 | 290,0 ± 7,98 | − 6,1 N.S. |

TABLE IV-continued

| TREAT-MENT | NUMBER OF RATS | WEIGHT OF THYMUS Mean (MG) ± e.s. | % AND PROB-ABILITIES |
|---|---|---|---|
| JO 1032 0,25 mg/pellet | 10 | 295,8 ± 11,52 | − 4,2 N.S. |
| JO 1032 1,25 mg/pellet | 10 | 309,6 ± 18,82 | + 0,3 N.S. |

N.S. insignificant

When administered in efficient dose for local antiinflammatory activity, compound JO 1032 is free of thymolytic properties.

(c - 2) Systemic Activity

The $ED_{50}$ for each products and corresponding steroids are indicated in the TABLES V and VI (the calculated $ED_{50}$ are the total dose administered during four days, per rat of about 50 grams).

TABLE V

| TREATMENT | DERIVATIVES OF PREDNISOLONE | |
|---|---|---|
| | ORAL ROUTE | SUB-CUTANEOUS ROUTE |
| Prednisolone (base) | 0.34 mg | 0.84 mg |
| Prednisolone (acetate) | 0.64 mg | 0.23 mg |
| JO 1007 | 9.6 mg | 30.4 mg |
| JO 1009 | — | 8 mg |
| JO 1014 | 40 mg | >40 mg |

When administered by oral route, the tested compounds exert a thymolytic activity which is 15 to 60 times less than that of prednisolone; when administered subcutaneously, this activity is 35 to 175 less than that of the reference compound.

TABLE VI

| DERIVATIVES OF PREDNISONE | |
|---|---|
| TREATMENT | ORAL ROUTE |
| Prednisone acetate | $ED_{50} = 2,9$ mg |
| JO 1032 | $ED_{50} > 750$ mg |

When administered by oral route in a total dose of 750 mg (i.e. 125 mg/rat/day) compound JO 1032 is free of thymolytic activity.

RATIO OF THE LOCAL ANTI-INFLAMMATORY ACTIVITY TO THE THYMOLYTIC ACTIVITY

The ratio of the local anti-inflammatory activity to the thymolytic activity is all the greater as these products possess a low antiinflammatory activity ($ED_{50}$ high in the numerator) and a large thymolytic activity ($ED_{50}$ low in the denominator).

The ratio is indicated in TABLES VII and VIII which follow:

TABLE VII

| DERIVATIVES OF THE PREDNISOLONE | |
|---|---|
| $ED_{50}$ Anti-proliferative activity / $ED_{50}$ thymolytic activity | |
| Thymolytic activity determined by the oral route | Thymolytic activity determined by sub-cutaneous route |
| Prednisolone (base): 12.5 | 5 |
| Prednisolone (acetate): 3 | 9 |
| JO 1007: 0.046 | 0.014 |
| JO 1009: — | 0.0625 |
| JO 1014: 0.012 | 0.0125 |

This chart shows that the compounds according to the invention exert a local antiproliferative activity and that they are free of systemic thymolytic properties.

TABLE VIII

| | $ED_{50}$ ANTI-PROLIFERATIVE ACTIVITY / $ED_{50}$ THYMOLYTIC ACTIVITY/ ORAL ROUTE |
|---|---|
| JO 1032 | < 0,0075 |

This chart shows that compound JO 1032 exerts a local antiinflammatory activity and no systemic thymolytic effect at the maximum dose tested.

(d) ACTION ON THE PROTEIN METABOLISM (d - 1) Local Action

The activity by local treatment is expressed in TABLE IX.

TABLE IX

| TREATMENT | INCREASE OF BODYWEIGHT MEAN (G) ± e.s. | % AND PROB-ABILITIES |
|---|---|---|
| CONTROL | 40,4 ± 2,09 | — |
| JO 1032 0.01 mg/pellet | 33,1 ± 1,90 | − 18,1 N.S. |
| JO 1032 0.05 mg/pellet | 40,1 ± 2,48 | − 0,7 N.S. |
| JO 1032 0,25 mg/pellet | 41,3 ± 1,36 | + 2,2 N.S. |
| JO 1032 1,25 mg/pellet | 35,5 ± 3,79 | − 12,1 N.S. |

When administered in efficient dose for local antiinflammatory activity, compound JO 1032 is free of proteolytic activity.

(d - 2) Systemic Activity

The increase of bodyweight are indicated in TABLE X.

TABLE X

| TREAT-MENT | INCREASE OF BODYWEIGHT MEAN (G) ± e.s. | % AND PROB-ABILITIES |
|---|---|---|
| CONTROL | 21,4 ± 1,00 | — |
| Prednisone acetate 0.1 mg/Rat/jour | 22,3 ± 0,94 | + 4,2 |
| Prednisone acetate 0,5 mg/Rat/jour | 18,6 ± 0,97 | − 13,1 |
| Prednisone acetate 2,5 mg/Rat/jour | 14,1 ± 1,11 | − 34,1 p<0,001 |
| Prednisone acetate 12,5 mg/Rat/jour | 5,2 ± 1,55 | − 75,7 p<0,001 |
| JO 1032 1 mg/Rat/jour | 25,8 ± 2,74 | + 20,6 N.S. |
| JO 1032 5 mg/Rat/jour | 25,5 ± 0,83 | + 19,2 p<0,01 |
| JO 1032 25 mg/Rat/jour | 22,9 ± 0,84 | + 7,0 N.S. |
| JO 1032 125 mg/Rat/jour | 19,4 ± 1,22 | − 9,4 N.S. |

Compound JO 1032 is free of systemic proteolytic activity, whereas prednisolor acetate exerts such an activity.

(e) ACTION ON THE ADRENALS

(e - 1) Local Effect

The local effect on the adrenals are summarized in TABLE XI.

TABLE XI

| TREATMENT | NUMBER OF RATS | ADRENAL WEIGHT (mg) MEAN ± e.s. | % AND PROBABILITIES |
|---|---|---|---|
| CONTROL | 10 | 25,8 ± 1,31 | — |
| JO 1032 0,01 mg/pellet | 10 | 27,2 ± 0,87 | + 5,4 N.S. |
| JO 1032 0,05 mg/pellet | 10 | 26,1 ± 0,62 | + 1,2 N.S. |
| JO 1032 0,25 mg/pellet | 10 | 25,4 ± 0,91 | − 1,6 N.S. |
| JO 1032 1,25 mg/pellet | 10 | 26,0 ± 1,04 | − 0,8 N.S. |

When administered in doses efficient on inflammatory granulomae, compound JO 1032 is free of adrenolytic activity.

(e - 2) Systemic Effect

The results are reported in the following TABLE XII.

TABLE XII

| TREATMENT | NUMBER OF RATS | ADRENAL WEIGHT (MG) MEAN ± e.s. | % AND PROBABILITIES |
|---|---|---|---|
| CONTROL | 10 | 28,1 ± 1,02 | — |
| PREDNISONE ACETATE 0,1 mg/Rat/jour | 10 | 27,6 ± 0,95 | − 1,8 N.S. |
| PREDNISONE ACETATE 0,5 mg/Rat/jour | 10 | 27,4 ± 1,04 | − 2,5 N.S. |
| PREDNISONE ACETATE 2,5 mg/Rat/jour | 10 | 22,9 ± 0,96 | −18,5 p <0,01 |
| PREDNISONE ACETATE 12,5 mg/Rat/jour | 10 | 22,0 ± 1,07 | −21,7 P <0,001 |
| JO 1032 1 mg/Rat/jour | 10 | 26,9 ± 0,77 | −4,3 N.S. |
| JO 1032 5 mg/Rat/jour | 10 | 27,2 ± 0,65 | − 3,2 N.S. |
| JO 1032 25 mg/Rat/jour | 10 | 25,5 ± 1,22 | − 9,3 N.S. |
| JO 1032 125 mg/Rat/jour | 10 | 26,1 ± 1,29 | − 7,1 N.S. |

When administered by oral route in a dose up to 125 mg/rat/day, compound JO 1032 is free of adrenolytic activity, whereas, in a dose 10 times less, prednisolone acetate exerts a highly significant adrenolytic activity.

POSOLOGY

The products described in the present invention are preferably utilized by local methods on the skin, the mucous membranes of the O.R.L. organ, the mucous membranes of the respiratory organs and the high and low digestive mucous.

The products are also used locally in the form of intra-articular injectable suspensions.

Generally speaking, the products are presented in the form of injectable, oral, nasal and auricular suspensions, of mouth-washes, gels and pomades, of suppositories, tablets and aerosols.

For the forms in which the product is in suspension, or may be considered as such, the active principle is utilized in the "micronized" form, the mean dimension of the particles being 2 microns.

The useful posology of the structures described by the present invention, as a function of their method of administration, extends between 0.25 and 50 mg. per unit taken and 1 to 200 mg. per day in adult animals.

The pharmaceutical forms may contain the products according to the invention, alone or associated with other therapeutic agents.

What we claim is:

1. New steroids compounds of the general formula:

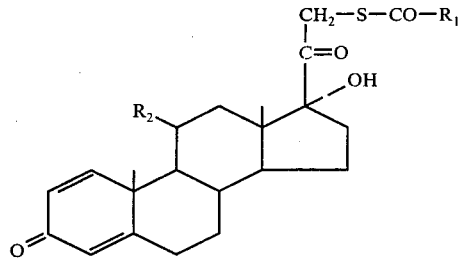

wherein:
$R_1$ is an alkyl radical having from 4 to 9 carbon atoms or is the p. fluorophenyl radical and $R_2$ is an hydroxyl radical or a ketone function.

2. The dihydroxy 11β, 17α thio-21 dioxo-3,20 pregnadiene-1,4 21-pivalate steroid compound of claim 1.

3. The dihydroxy 11β, 17α thio-21 dioxo-3,20 pregnadiene-1,4 21-heptanoate steroid compound of claim 1.

4. The dihydroxy 11β, 17α thio-21 dioxo-3,20 pregnadiene-1,4 21-decanoate steroid compound of claim 1.

5. The dihydroxy 11β, 17α thio-21 dioxo-3,20 pregnadiene-1,4 21-p. fluorobenzoate steroid compound of claim 1.

6. The dihydroxy 11β, 17α thio-21 dioxo-3,20 pregnadiene-1,4 21-pentanoate steroid compound of claim 1.

7. The dihydroxy 11β, 17α thio-21 dioxo-3,20 pregnadiene-1,4 21-methyl-2 butanoate steroid compound of claim 1.

8. The dihydroxy 11β, 17α thio-21 dioxo-3,20 pregnadiene-1,4 21-methyl-3 butanoate steroid compound of claim 1.

9. The dihydroxy 11β, 17α thio-21 dioxo-3,20 pregnadiene-1,4 21-hexanoate steroid compound of claim 1.

10. The dihydroxy 11β, 17α thio-21 dioxo-3,20 pregnadiene-1,4 21-methyl-4 pentanoate steroid compound of claim 1.

11. The dihydroxy 11β, 17α thio-21 dioxo-3,20 pregnadiene-1,4 21-dimethyl 3,3 butanoate steroid compound of claim 1.

12. The dihydroxy 11β, 17α thio-21 dioxo-3,20 pregnadiene-1,4 21-ethyl-2 butanoate steroid compound of claim 1.

13. The dihydroxy 11β, 17α thio-21 dioxo-3,20 pregnadiene-1,4 21-octanoate steroid compound of claim 1.

14. The dihydroxy 11β, 17α thio-21 dioxo-3,20 pregnadiene-1,4 21-ethyl-2 hexanoate steroid compound of claim 1.

15. The dihydroxy 11β, 17α thio-21 dioxo-3,20 pregnadiene-1,4 21-nonanoate steroid compound of claim 1.

16. The hydroxy-17α thiol-21 trioxo-3,11,20 pregnadiene-1,4 21-pivalate steroid compound of claim 1.

17. The hydroxy-17α thiol-21 trioxo-3,11,20 pregnadiene-1,4 21-heptanoate steroid compound of claim 1.

18. The hydroxy-17α thiol-21 trioxo-3,11,20 pregnadiene-1,4 21-decanoate steroid compound of claim 1.

19. The hydroxy-17α thiol-21 trioxo-3,11,20 pregnadiene-1,4 21-p. fluorobenzoate steroid compound of claim 1.

20. The hydroxy-17α thiol-21 trioxo-3,11,20 pregnadiene-1,4 21-pentanoate steroid compound of claim 1.

21. The hydroxy-17α thiol-21 trioxo-3,11,20 pregnadiene-1,4 21-methyl-2 butanoate steroid compound of claim 1.

22. The hydroxy-17α thiol-21 trioxo-3,11,20 pregnadiene-1,4 21-methyl-3 butanoate steroid compound of claim 1.

23. The hydroxy-17α thiol-21 trioxo-3,11,20 pregnadiene-1,4 21-hexanoate steroid compound of claim 1.

24. The hydroxy-17α thiol-21 trioxo-3,11,20 pregnadiene-1,4 21-methyl-4 bentanoate steroid compound of claim 1.

25. The hydroxy-17α thiol-21 trioxo-3,11,20 pregnadiene-1,4 21-dimethyl-3,3 butanoate steroid compound of claim 1.

26. The hydroxy-17α thiol-21 trioxo-3,11,20 pregnadiene-1,4 21-ethyl-2 butanoate steroid compound of claim 1.

27. The hydroxy-17α thiol-21 trioxo-3,11,20 pregnadiene-1,4 21-octanoate steroid compound of claim 1.

28. The hydroxy-17α thiol-21 trioxo-3,11,20 pregnadiene-1,4 21-ethyl-2 hexanoate steroid compound of claim 1.

29. The hydroxy-17α thiol-21 trioxo-3,11,20 pregnadiene-1,4 21-nonanoate steroid compound of claim 1.

* * * * *

UNITED STATES PATENT AND TRADEMARK OFFICE
CERTIFICATE OF CORRECTION

PATENT NO. : 4,098,804

DATED : July 4, 1978

INVENTOR(S) : Dieran Robert Torossian, et al.

It is certified that error appears in the above-identified patent and that said Letters Patent are hereby corrected as shown below:

Column 1, line 25 delete [in which:].

Column 2, line 52 delete [satisfied] and insert salified therefor.

Column 3, line 62 delete [320] and insert 3.20 therefor.

Column 4, line 47 delete [cu.em.] and insert cu. cm. therefor.

Column 5, line 62 delete [sodium], second occurrence, and insert solution therefor.

Column 6, line 11 delete [EXAMPLe] and insert EXAMPLE therefor.

line 12, delete [THIOL -3,11,20 PREGNADIENE] and insert THIOL - 21   TRIOXO - 3,11,20 PREGNADIENE therefor.

lines 26 and 27 delete [the-romether] and insert thermometer therefor.

Column 7, line 16 delete [THIOL described 21] and insert THIOL - 21 therefor.

column 10, line 40 delete [implanation] and insert implantation therefor.

UNITED STATES PATENT AND TRADEMARK OFFICE
CERTIFICATE OF CORRECTION

PATENT NO. : 4,098,804
DATED : July 4, 1978
INVENTOR(S) : Dieran Robert Torossian, et al.

It is certified that error appears in the above-identified patent and that said Letters Patent are hereby corrected as shown below:

Column 11, line 48 delete [implanation] and insert implantation therefor.

Column 12, after "TABLE I" and before "(a - 2) Systemic Anti-inflammatory Activity" insert In considering the dry weight of the granulomae, it is clear that local antiinflammatory activities of the various compounds are 6 to 10 times greater than the activity of the reference compond, prednisolone acetate Column 12, In "TABLE II", first column, beneath "Prednisone acetate" insert mg Rat.

Column 13, In "Table V" after "Derivatives of Prednisolone" correct the heading to read as follows:

TREATMENT    ORAL ROUTE    SUB-CUTANEOUS ROUTE

Column 14, In "TABLE X" line 12, delete [2,5 mg/Rat/jour].

Signed and Sealed this

Sixth Day of February 1979

[SEAL]

Attest:

RUTH C. MASON
*Attesting Officer*

DONALD W. BANNER
*Commissioner of Patents and Trademarks*